(12) United States Patent
Arumugam et al.

(10) Patent No.: US 9,228,972 B2
(45) Date of Patent: Jan. 5, 2016

(54) ELECTROANALYTICAL SENSOR BASED ON NANOCRYSTALLINE DIAMOND ELECTRODES AND MICROELECTRODE ARRAYS

(71) Applicant: Advanced Diamond Technologies, Inc., Romeoville, IL (US)

(72) Inventors: Prabhu U. Arumugam, Ruston, LA (US); Shabnam Siddiqui, Naperville, IL (US); John Carlisle, Romeoville, IL (US)

(73) Assignee: Advanced Diamond Technologies, Inc., Romeoville, IL (US)

( * ) Notice: Subject to any disclaimer, the term of this patent is extended or adjusted under 35 U.S.C. 154(b) by 407 days.

(21) Appl. No.: 13/775,015

(22) Filed: Feb. 22, 2013

(65) Prior Publication Data

US 2013/0213823 A1 Aug. 22, 2013

Related U.S. Application Data

(60) Provisional application No. 61/602,032, filed on Feb. 22, 2012.

(51) Int. Cl.
*G01N 27/327* (2006.01)

(52) U.S. Cl.
CPC .................................. *G01N 27/3278* (2013.01)

(58) Field of Classification Search
CPC .......... G01N 27/3271; G01N 27/3272; G01N 27/3278; G01N 27/403
See application file for complete search history.

(56) References Cited

U.S. PATENT DOCUMENTS 7,771,823 B2* 8/2010 Chaffin, III ................... 428/408
2011/0308942 A1* 12/2011 Liu et al. ....................... 204/400

* cited by examiner

*Primary Examiner* — Alexander Noguerola
(74) *Attorney, Agent, or Firm* — Locke Lord LLP; Christopher J. Capelli

(57) ABSTRACT

A diamond electrode and a diamond microelectrode array for biosensors and electroanalytical applications, such as electrochemical impedance spectroscopy (EIS), are disclosed. The electrode comprises a layer of ultra-smooth conductive nanocrystalline diamond (NCD) having a resistivity of >0.05 $\Omega$cm and a surface roughness of <20 nm $R_a$. Preferably, the diamond layer comprises boron or nitrogen-doped ultrananocrystalline diamond (UNCD) having an average grain size <10 nm and a surface roughness <10 nm $R_a$. It may be patterned to define a microelectrode array with a plurality of individually addressable electrodes, each having a diameter in the range from 100 nm to 100 μm. The surface of each microelectrode is hydrogen-terminated before bio-functionalization, i.e. modifying with sensing molecules for detection of a specific biological or chemical target and coating with a blocker for reducing non-specific binding. These diamond electrodes exhibited substantial increases in sensitivity, selectivity and signal reproducibility, e.g. for detection of *E. coli* K12 using EIS.

25 Claims, 16 Drawing Sheets

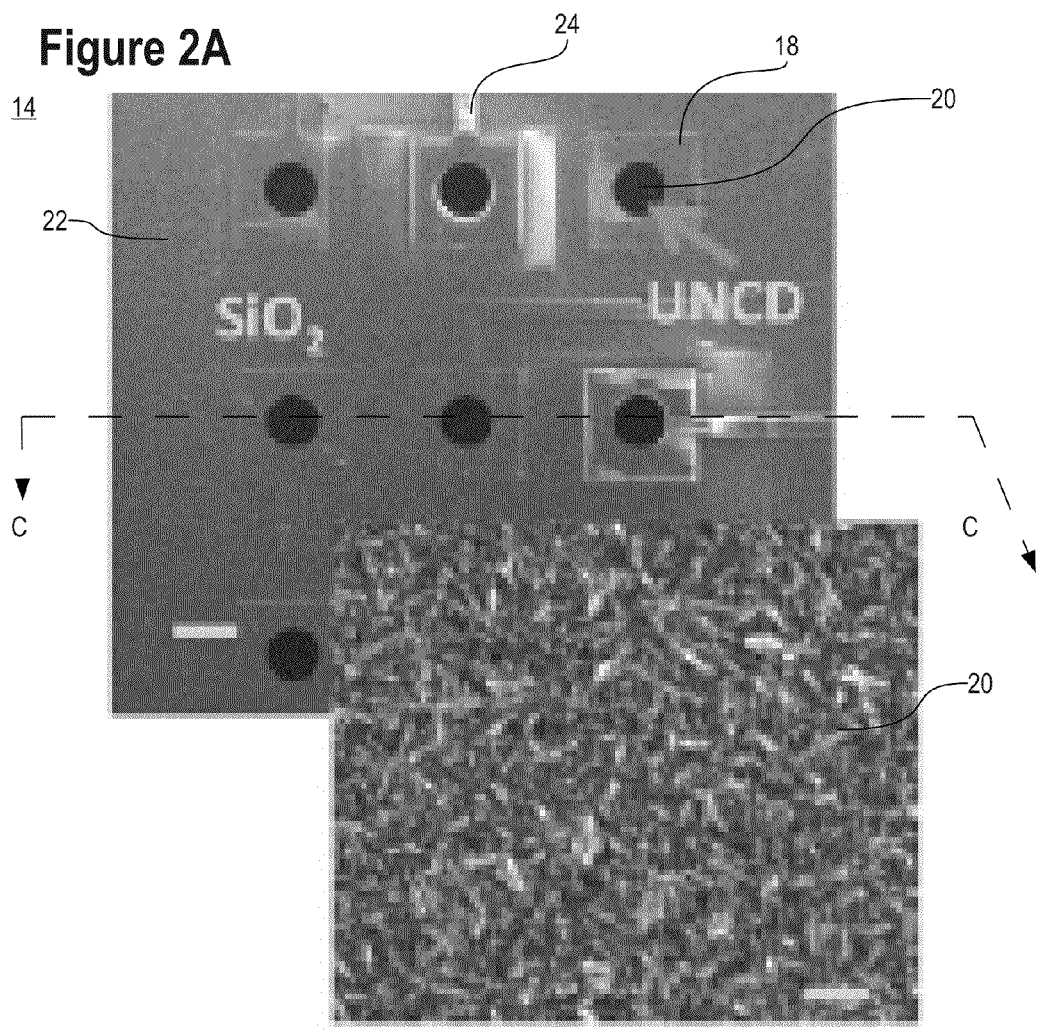
Figure 2A
Figure 2B
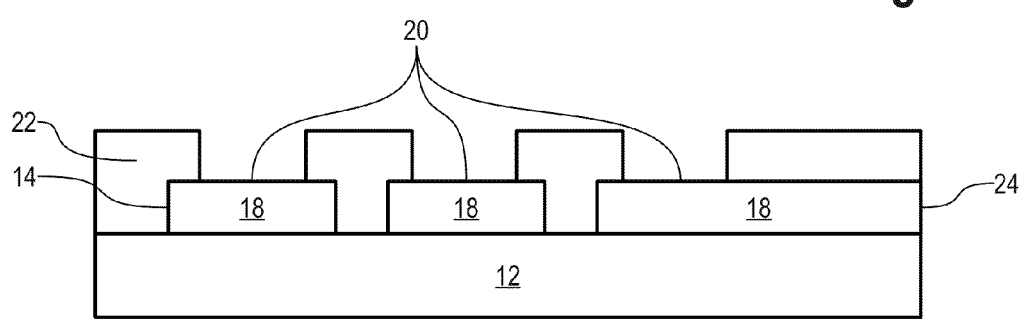
Figure 2C

ELECTROANALYTICAL SENSOR BASED ON NANOCRYSTALLINE DIAMOND ELECTRODES AND MICROELECTRODE ARRAYS

CROSS-REFERENCE TO RELATED APPLICATIONS

This application claims priority from U.S. provisional patent application Ser. No. 61/602,032, entitled "A Highly Robust Electroanalytical Platform Based on Nanocrystalline Diamond Arrays" filed Feb. 22, 2012. This application is incorporated herein by reference, in its entirety.

TECHNICAL FIELD

This invention relates to electrodes and microelectrode arrays for electroanalytical sensors for detection of biological and chemical targets, and more particularly relates to microelectrode arrays for electrochemical impedance spectroscopy (EIS).

BACKGROUND ART

It is desirable to have low-cost, specific and sensitive electroanalytical biosensors that can rapidly detect antigens in real-time, for applications such as remote environmental monitoring and point-of-care diagnostics. In electrochemical or electroanalytical sensors, the binding or capture of a target molecule on a modified electrode surface is detected electrically, e.g. by changes in interfacial resistance (i.e. impedance transduction), by the reaction of redox molecules to generate current (i.e. amperometric or enzymatic transduction), and detection of changes in conductivity by other means. For example, electrochemical impedance spectroscopy (EIS) provides a basis for biosensors that can be used to detect a wide variety of antigens, including bacteria, DNA, and proteins.

However, commercial development of such sensors has been hindered by issues such as poor signal to noise ratios, resulting in difficulty in interpreting a change in impedance on antigen binding and poor signal reproducibility as a result of surface fouling and non-specific binding.

Electrodes for such biosensors may comprise conductive surfaces that are modified with suitable layer(s) of biological materials—such as antibodies, nucleic acids or enzymes; or non-biological materials, e.g. synthetic materials—such as aptamers and polymer membranes. Selective and sensitive detection of various biomolecules and chemicals (e.g. bacteria, nucleic acids, whole cells, proteins, toxins, biomarkers, neurotransmitters, drugs, hormones, cytokines, chemokines, growth factors) has been previously demonstrated. Much research has been performed using electrodes comprising noble metals, typically platinum (Pt) or gold (Au), and conductive $sp^2$ carbon materials such as graphite, Highly Oriented Pyrolytic Graphite (HOPG), glassy carbon and various semiconductor materials.

When modifying electrode surfaces with recognition molecules using covalent immobilization chemistries, most surfaces (Pt, Au, silicon and non-conductive silica glass slides) are not hydrolytically stable and thus oxidize the recognition molecules that are critical to detect targets selectively. For metals with high electrical conductivity, the background currents are generally high because their surfaces oxidize easily, which affect the sensitivity of detection. Other disadvantages of metal electrodes are the introduction of background noise at the micro-scale and the nano-scale and also they become inactive relatively rapidly in aqueous-based samples due to surface oxidation.

Typically, to achieve reliable and reproducible detection of target species, multiple measurements are required. This requires more than one electrode modified with or without recognition molecules that specifically bind to targets or mismatch molecules/probes (e.g. mismatch base pairs in oligonucleotides) that measures the degree of cross hybridization, or how much lower the detection signals for noise are and are "subtracted" from the perfect match probe. To detect more than one target in a sample (called multiplexing), multiple electrodes are required. For example, to detect two types of bacteria in a sample, at least two electrodes are required, i.e. each modified with a different specific (also called "selective") sensing molecule. So, for multiplexing and for improved sensitivity of detection, an array of electrodes, usually patterned on the substrate, is required.

It has also been shown that by micro-patterning and nano-patterning a conductive electrode surface, the sensitivity is greatly improved. This is due to decreases in background (also called charging) current, which is directly proportional to electrode area. Thus micro-electroanalytical platforms based on microelectrode arrays comprising tens or hundreds of electrodes are known, and conventionally microelectrode materials comprise highly conductive metals such as platinum and gold.

It is recognized that conductive diamond electrodes, e.g. boron-doped diamond, are more resistant to oxidation. Thus, diamond microelectrode arrays potentially offer advantages over conventional metal electrodes with respect to oxidation. However, microcrystalline diamond (MCD) electrodes typically have significantly higher surface roughness (typically >100 nm $R_a$) relative to metal surfaces. High surface roughness generally increases nonspecific binding, limits selectivity, and increases the background charging current, which is proportional to the microscopic electrode area. A higher background charging current further limits sensitivity.

It would therefore be desirable to provide improved or alternative electrodes and microelectrode arrays for electroanalytical sensors and methods for electrochemical detection of biomolecules with improved sensitivity, for example, for EIS based biosensors.

SUMMARY OF THE INVENTION

The present invention seeks to overcome one or more disadvantages of known electrodes for electroanalytical platforms, particularly for systems and methods based on electrochemical biosensors comprising diamond electrodes and diamond microelectrode arrays.

Thus one aspect of the present invention provides an electroanalytical sensor comprising at least one electrode, said electrode comprising: a layer of conductive nanocrystalline diamond (NCD) having a resistivity of >0.05 Ωcm and an (ultra-smooth) surface having surface roughness of <20 nm $R_a$ (arithmetic mean value).

The diamond layer preferably comprises ultrananocrystalline diamond (UNCD) having an ultra-smooth as-deposited surface, i.e. having a surface roughness <10 nm $R_a$, and more preferably ultrananocrystalline (UNCD) diamond having an average grain size of <10 nm and a surface roughness of <10 nm $R_a$.

To provide the required level of conductivity, the NCD or UNCD layer is moderately doped (say up to 3000 ppm), i.e. with boron or nitrogen, i.e. to provide the required resistivity of >0.05 Ωcm.

It is observed that a NCD or UNCD diamond electrode or microelectrode having lower conductivity provides improved sensitivity for electroanalysis, e.g. EIS for detection of bacteria or other biomolecules.

The improvement in sensitivity is believed to be due to the influence of the electrical conductivity and the chemical composition of the grain and grain boundaries of the electrode on electron transfer kinetics, which in turn influences the exchange current of the biosensor electrochemical system. The lower conductivity is believed to provide slower electron transfer kinetics and smaller magnitudes of exchange currents of UNCD and NCD as compared to metal electrodes. Thus, the UNCD and NCD surfaces are more electrochemically stable over a wide range of electrochemical potentials, which makes UNCD and NCD less susceptible to generating electrical background noise, and enables a higher peak signal voltage to be used. It is also believed that the ultra-smooth UNCD surface reduces nonspecific binding, improves selectivity, and reduces the background charging current. A lower background charging current further improves sensitivity. Moreover, since diamond is more highly resistance to oxidation and fouling than conventional metal electrodes used for biosensors, a NCD or UNCD electrode or microelectrode array provides a significantly more robust electro-analytical platform for applications such as EIS.

Depending on the electroanalytical application, the electrode may comprise a single larger area electrode or the diamond layer may be patterned to define a microelectrode array, e.g. a plurality of 10s or 100s of microelectrodes, e.g. of 200 μm diameter or less. For some applications the electrodes may have an active area of diameter or lateral dimension in the range 1 mm or less; or 100 μm or less; or 100 nm to 10 μm. The diameter or dimension is matched to the size of a biological or chemical target, e.g. a bacterium or biomolecule to be detected.

The diamond layer typically has a thickness of 500 nm or more. Typically, the spacing between the microelectrodes is between 1 and 6 times said diameter or lateral dimension of the microelectrodes. The number of microelectrodes may be between 1 and 10,000. Conductive interconnections may be provided for electrically addressing each microelectrode individually.

The microelectrode array may comprise a non-conductive dielectric passivation layer overlying the patterned layer of ultrananocrystalline diamond, with apertures defined in the passivation layer over each microelectrode, i.e. to define the active area of each electrode. For electrochemical or electroanalytical methods, such as EIS, the passivation layer may have a thickness of, e.g. 100 nm to 1000 nm, and may have a thickness sufficient to define a cell or micro-container for electrolyte for each microelectrode. For example, the passivation layer may comprise, non-conductive diamond; an oxide or nitride; or polymers selected from the group consisting of PDMS, SU-8, parylene and other suitable polymers.

The exposed surface of diamond layer forming each electrode is surface treated to provide either a hydrogen, oxygen or a combination of hydrogen and oxygen terminated surface.

For use in a biosensor, such as an EIS based biosensor, the hydrogen terminated surface is bio-functionalized. For example, the hydrogen terminated surface further comprises a surface modification comprising attachment of sensing molecules for detection of a specific target molecule and a coating of a blocking layer for reducing non-specific binding of the target molecule.

In one exemplary embodiment, the diamond electrode comprises a UNCD diamond microelectrode array for detection of an E. coli bacterium by electrochemical impedance spectroscopy, wherein the sensing molecules comprise an E. coli antibody and the blocking layer comprises a casein blocking layer. Reliable detection of E. coli K12 with high sensitivity was demonstrated, potentially with a detection limit comparable to most immunoassays.

Another aspect of the invention provides a microelectrode array for an electroanalytical biosensor comprising a plurality of microelectrodes, each microelectrode comprising a layer of conductive nanocrystalline diamond (NCD) having a resistivity of >0.05 Ωcm and a surface roughness of <20 nm $R_a$. The diamond layer is preferably boron or nitrogen doped nanocrystalline diamond having an average grain size of <10 nm and surface roughness <10 nm Ra. The diamond surface is preferably hydrogen terminated and may be biofunctionalized.

Also provided is a method of fabricating a microelectrode array for an electrochemical biosensor, comprising: providing a substrate; providing thereon a layer of conductive diamond comprising nanocrystalline diamond having a resistivity of >0.05 Ωcm and a surface having a surface roughness of <20 nm $R_a$, patterning the diamond layer to define a plurality of microelectrodes; depositing thereon a dielectric passivation layer and opening apertures in the passivation layer over each microelectrode to expose the surface of each microelectrode; surface treating each microelectrode to provide a hydrogen terminated surface.

A further aspect of the invention comprises a method of electrochemically sensing a target by electrochemical impedance spectroscopy using a sensor comprising a diamond microelectrode array, wherein sensing comprises detecting an impedance indicative of the presence or absence of the target biomolecule on the electrode by application of a signal having an peak amplitude in the range from 10 mV to 100 mV at frequency in the range from 1 Hz to 750 kHz and preferably in the range from 10 Hz to 500 Hz.

A higher voltage is required for detection of small molecules, and the microelectrode array comprising UNCD microlectrodes having a resistivity of >0.05 Ωcm and a surface roughness of <20 nm $R_a$ provides a low-noise microelectrode array that can be used at a higher peak signal voltage, i.e. a peak signal amplitude of >25 mV, >50 mV or up to 100 mV to provide sufficient sensitivity to detect smaller target molecules.

For a given geometric area, UNCD and NCD surfaces exhibit lower background currents, i.e. at least 10× lower, and thus exhibit improved sensitivity, compared to conventional metal electrodes. For example, for electrochemical impedance spectroscopy (EIS) with a NCD or UNCD microelectrode array having 100 μm diameter electrodes, even though the electrodes are small, a signal-to-noise ratio of greater than 300 can be achieved.

Thus, diamond electrodes and microelectrode arrays for electroanalytical systems are provided, which mitigate one or more of the problems mentioned above, or provide one or more advantages, such as, improved sensitivity, selectivity, signal to noise ratio, signal reproducibility.

The foregoing and other objects, features, aspects and advantages of the present invention will become more apparent from the following detailed description, taken in conjunction with the accompanying drawings, of preferred embodiments of the invention, which description is by way of example only.

BRIEF DESCRIPTION OF THE DRAWINGS

FIG. 2A shows a SEM (Scanning electron microscope) image of one 3×3 UNCD MEA of the embodiment, showing the nine 200-µm diameter electrodes and part of respective conductive traces providing interconnections to contact pads (not shown); FIG. 2B shows an SEM of the surface morphology of the ultrasmooth UNCD surface; FIG. 2C shows a schematic cross sectional view through the MEA of FIG. 2A;

DETAILED DESCRIPTION OF THE EMBODIMENTS

Figures 1A, 1B:
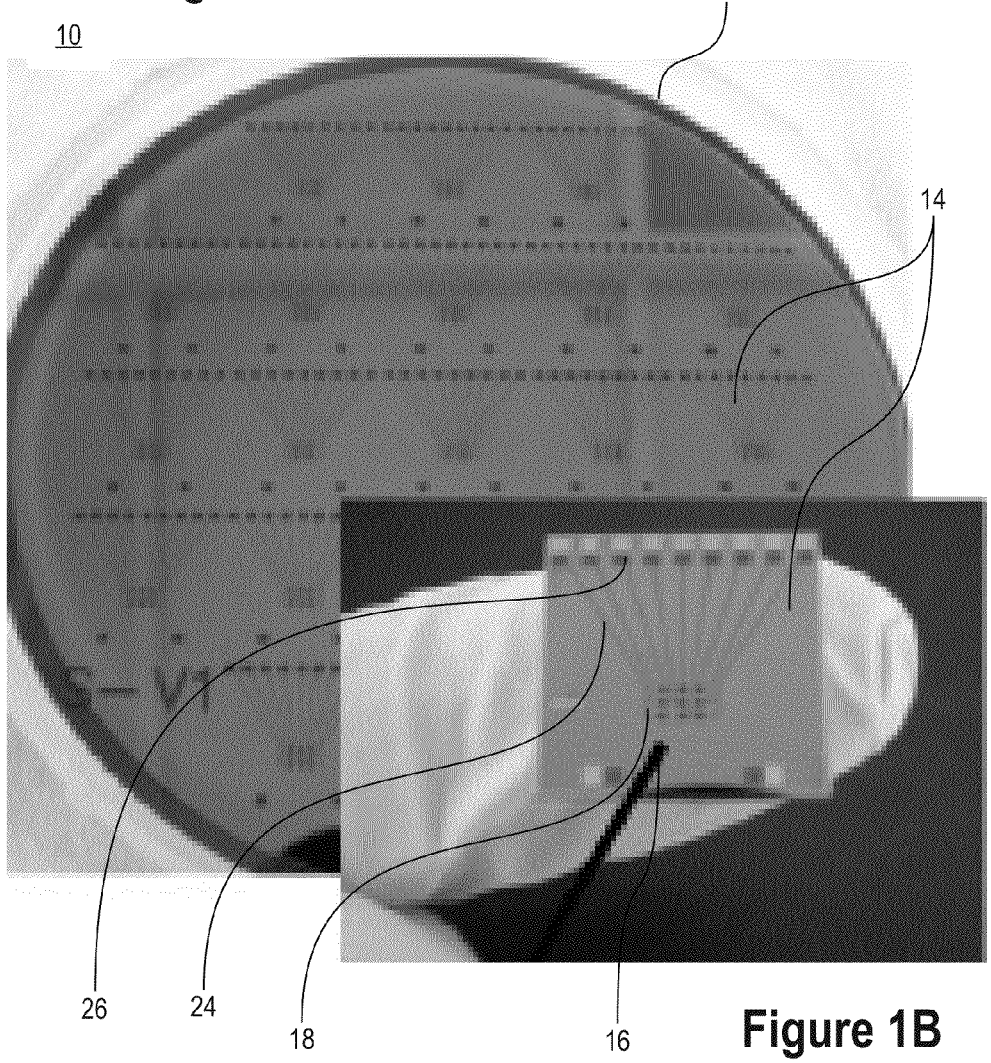
FIG. 1A shows an optical image of a 4 inch silicon wafer having fabricated thereon a plurality of die, each comprising a 3×3 UNCD microelectrode array (MEA) according to an embodiment of the invention; wherein each microelectrode is 200 µm in diameter.
FIG. 1B shows an enlarged view of one die.

FIG. 1A shows an optical image of a substrate comprising a 4 inch wafer 10 comprising a silicon substrate 12 having fabricated thereon a plurality of chips or die 14, each comprising a 3×3 UNCD microelectrode array (MEA) 16, according to an embodiment of the present invention. In this example, as shown enlarged in FIG. 1B, each microelectrode 18 has an active area 200-µm in diameter and conductive traces 24 are provided to individually connect each microelectrode to a respective contact pad 26. FIG. 2A shows a SEM image of part of one of the chips 14 showing an enlarged view of the nine individually addressable microelectrodes 18 of the MEA 16, with the overlying passivation layer 22 having apertures over each electrode. A SEM image showing the ultrasmooth UNCD surface morphology is shown in FIG. 2B.

As shown in FIG. 2C, which shows a cross-section C-C through the MEA 16 shown in FIG. 2A, the MEA is fabricated on a silicon substrate 12 on which is formed a dielectric layer, e.g. silicon dioxide 13. A diamond layer 14 comprising UNCD is formed thereon and patterned to define the microelectrodes 18. Optionally, a metal layer (not shown) may be provided under the UNCD electrode layer to form the conductive traces 24 and contact pads 26, or the latter may also be formed from the UNCD layer as illustrated. The UNCD layer preferably is boron or nitrogen doped to provide a resistivity greater than 0.05 Ω-cm, an average grain size of 10 nm, and an ultra-smooth surface, i.e. having a surface roughness of <20 nm Ra, and preferably <10 nm Ra. The overlying dielectric passivation layer 22 is deposited over the diamond layer 14, and apertures are opened over each microelectrode 14 to expose the surface 20 of each microelectrode. The surface 20 of each microelectrode is surface treated to provide a hydrogen terminated UNCD surface.

Details of the fabrication and characterization of a microelectrode array (MEA) comprising a plurality of diamond electrodes according to a first embodiment of the invention are disclosed in a recent publication by the inventors and co-authors entitled "A quantitative study of detection mechanism of a label-free impedance biosensor using ultrananocrystalline diamond microelectrode array" by Siddiqui, Shabnam, et al., published in Biosensors and Bioelectronics (2012), on which the following description is based, and this publication is incorporated herein by reference in its entirety.

UNCD Microarray Fabrication

Four inch silicon wafers with a surface coating of 1 µm-thick thermal SiO2 (Wafer World) were used to grow a 2 µm-thick UNCD film. The electrical resistivity of the film was >0.05 Ωcm based on 4-probe measurements (Pro4, Lucas Labs, Gilroy, Calif.). The average roughness of the UNCD film was <10 nm rms based on AFM measurements (Digital Instruments, Santa Barbara, Calif.). Optical microlithography was used to fabricate 21 chips per wafer. Each chip was micro patterned into nine individually address-able 200 µm diameter disk microelectrodes in a 3×3 array format.

Briefly, the micro fabrication steps were as follows: (a) deposit a 500 nm thick SiO2 layer using Plasma Enhanced CVD (PECVD); (b) pattern oxide using a 1.7 µm thick positive resist; (c) wet etch the oxide in 10:1 Buffered Oxide Etchant for 15 min; (d) dry etch the UNCD with reactive ion etching (ICP-RIE) of O2/SF6 gas mixture (Moldovan et al., 2009) through the oxide hard mask formed in the previous steps to form MEAs, electrical contact pads and the electrical lines between them; (e) deposit another 500 nm thick SiO2 PECVD film; and (f) wet etch SiO2 to open up the UNCD microelectrode (200 µm diameter) array and the contact pads. The final SiO2 film was 1 µm thick and found to be adequate to passivate the underlying UNCD form the electrolyte solution.

Surface characterization using SEM and optical microscopy showed no major defects and/or contamination of the electrode surface. The UNCD electrode surface is more oxidized and hydrophilic than the as-deposited surface. This is because the surface is exposed with strongly oxidizing chemicals during micro fabrication and acquires hydrophilic groups. To achieve higher efficiencies during photochemical grafting of biomolecules, the surface is preferentially hydrogen terminated by exposing the UNCD surface to an atomic hydrogen environment in HFCVD chamber for 15 min at 8 Torr.

Electro-Analytical System

Figure 3:
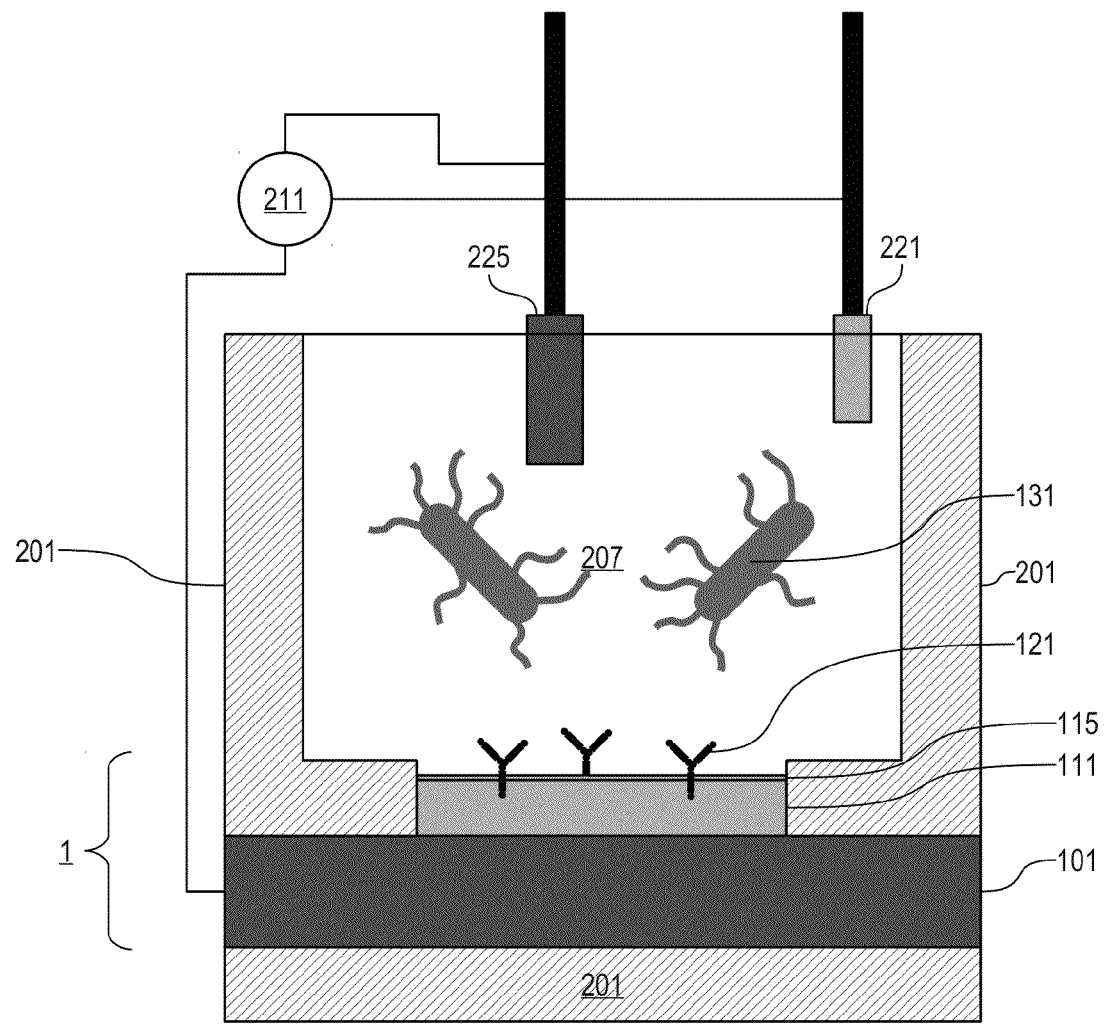
FIG. 3 shows a schematic diagram representing a simple electrochemical cell of an electro-analytical biosensor comprising a UNCD microelectrode according an embodiment of the present invention.

FIG. 3 shows a schematic diagram of a simple apparatus comprising one microcell of a biosensor comprising a diamond microelectrode for electrochemical impedance spectroscopy, for detection of a biological or chemical target, e.g. a biomolecule or bacteria. A first electrode 101 (working electrode or anode), supplied by a power source 211, comprises a layer of conductive diamond wherein the surface is modified with suitable molecules for selective binding of a target, e.g. a biomolecule or bacteria, for detection or surface studies. The electrode 221 (cathode) is primarily used as a counter electrode (usually a platinum wire) and a third electrode 225 is used a reference (usually a Ag/AgCl or saturated calomel electrode). The working electrode, i.e. diamond microelectrode 101 comprises a layer of NCD, while the cathode electrode 221 may be comprised of noble metals such as platinum or gold as wire, sheet or a patterned thin film deposited by physical vapor deposition. The conductive NCD layer is boron-doped or nitrogen doped diamond to provide a resistivity of >0.05 Ωcm. In the preferred embodiment, the NCD layer comprises UNCD having an average grain size less than 10 nm and a surface roughness of <20 nm Ra or preferably <10 Ra.

As illustrated schematically in FIG. 3, each cell takes the form of a container or cell 201 having a base and walls containing an electrolyte 207. The electrolyte 207 contains the target molecules 131 to be detected by the electrochemical sensing electrode 101.

Figure 4:
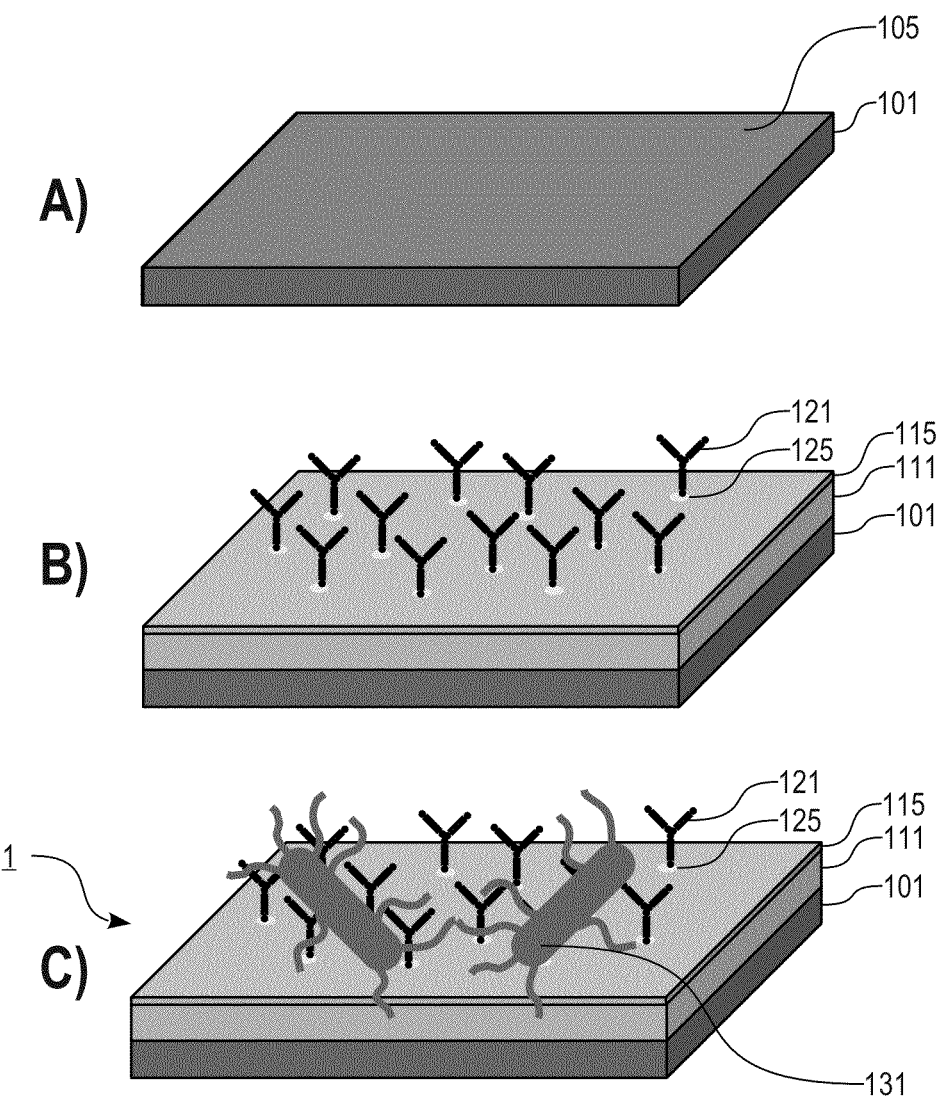
FIG. 4 shows an enlarged schematic view part of a UNCD microelectrode of an electroanalytical biosensor, illustrating the principle of using electrochemical impedance spectroscopy for sensing the presence or absence of a biological or chemical target by a change of impedance at the electrode: A) an electrode surface of the electrochemical biosensor before surface functionalization; B) the modified electrode surface before bacteria capture; and C) the modified surface after bacteria capture.

FIG. 4 illustrates schematically the principle of electrochemical detection of a target by electrochemical impedance spectroscopy using the UNCD microelectrodes. FIG. 4 shows an enlarged schematic view of an area of an electrode of an electrochemical biosensor such as shown in FIG. 3, illustrating A) an electrode surface of the electrochemical biosensor before surface functionalization; B) the modified electrode surface before bacteria capture; and C) the modified surface after bacteria capture. The bare electrode 101 is shown in FIG. 4a. This electrode 101 may optionally comprise a metal substrate (not shown) having good electrical conductivity on which the layer of NCD or UNCD is deposited. The electrode surface 105 is modified, as shown in FIG. 4b, with suitable molecules for specific detection. The surface modification 111 is achieved by known physical, chemical, photochemical and/or electrochemical means. As an example, to illustrate the effectiveness of the MEA of the embodiment for detection of a biological target by EIS, the electrode surface 105 is modified with antibodies for E. coli capture and detection.

A blocking layer 115 (casein, BSA, or a mixture of casein and BSA) can be coated after antibody 121 immobilization to reduce nonspecific binding of target 131 and other interferents from the sample. The charge transfer resistance that arises due to resistance to the exchange of electrons between electrode and $Fe(CN)_6^{3-/4-}$ redox couple in the pores 125 where antibodies are immobilized. It is in the pores 125 that the bare electrode surface is exposed to electrolyte and electron transfer between electrode and $Fe(CN)_6^{3-/4-}$ redox couple takes place.

Figure 5:
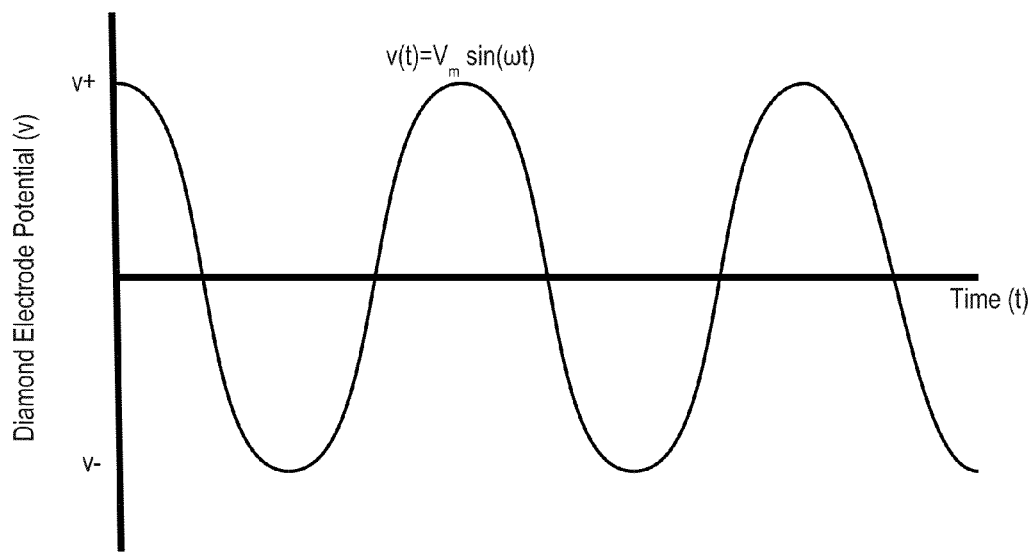
FIG. 5 shows a graph of a representative sinusoidal voltage signal applied to the UNCD electrode for electrochemical impedance spectroscopy.

FIG. 4c shows the target bacteria 131 binding to the antibodies 121. The presence or absence of the target 131 may be determined by electrical measurements, e.g. by using electrochemical impedance spectroscopy (EIS) to detect a change in impedance when the target is captured Electrochemical Impedance Spectroscopy For EIS based biosensors, an alternating voltage, i.e. a sinusoidal input signal $v(t)=V_m \sin(\omega t)$ (as shown in FIG. 5), is applied to the electrode 101 and the resulting current $i(t)=I_m \sin(\omega t+\theta)$ is measured (where $V_m$ is the voltage amplitude, $\omega$ is the frequency, $I_m$ is the current amplitude, and $\theta$ is the phase). The ratio $v(t)/i(t)$ at a particular frequency is defined as the impedance (Z) of the cell. This measurement is repeated at different frequencies, yielding $Z(\omega)$. The electrode-cell system behavior is then investigated by fitting experimental impedance data to an equivalent circuit model.

In EIS biosensors, the change in impedance after antigen binding to the bio-functionalized electrode surface that is modified with monolayers and receptors (oligonucleotide, DNA, antibody, aptamer) is typically interpreted as detection.

Once the detection is complete, the microelectrodes can be refreshed using 0.1M glycine-HCl buffer (pH 2.1) so that the same array can be reused up to 10 times and in some cases, more than 10 times.

Several experiments were performed with UNCD microarrays according to embodiments of the invention, demonstrating the high reproducibility of detected signals on the modified diamond electrode.

To use MEAs for multiplexing, i.e. to detect or to study different targets, the microelectrodes in the array are selectively coated with suitable recognition molecules using a spotting technique. The spotting technique allows no cross contamination of any two antibodies between the microelectrodes in a UNCD array. A further embodiment may include using spotting techniques to selectively spot linker molecules such as dodecene/TFAAD mixture and glutaraldehyde directly on the array. This allows more control over where antibodies will be immobilized (in this case only on the microelectrode surface), which should minimize nonspecific binding and thus, generate highly reproducible signals after target binding.

Figure 6:
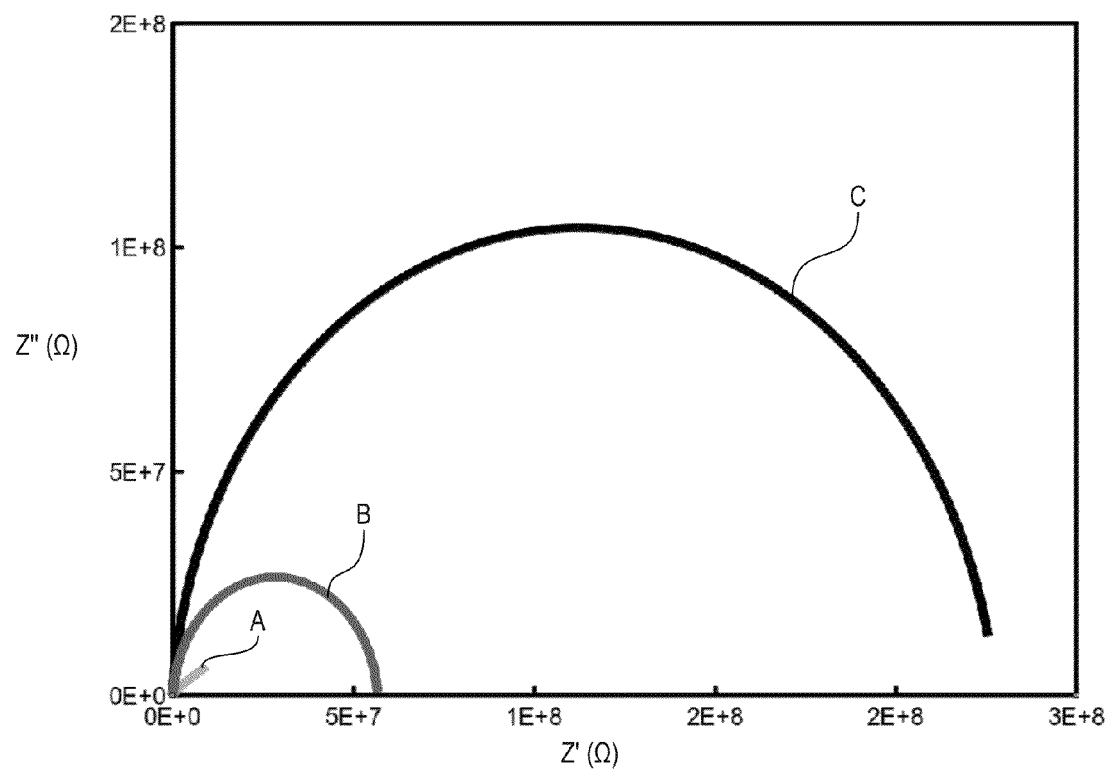
FIG. 6 shows EIS Nyquist plots for the UNCD electrode A) before surface functionalization; B) after surface modification and before bacteria capture; C) and the modified surface after bacteria capture.

FIG. 6 shows Nyquist plots of the EIS of the microelectrode: Line A represents the UNCD electrode 101 prior to treatment. The modified electrode, i.e. after antibody and casein blocker deposition is represented by line B and line C is after bacteria capture. The x-axis represents the real impedance (Z') of the EIS while the y-axis is the imaginary component of the impedance (Z"). These plots each form a substantially semi-circular spectrum, wherein the diameter of the semi-circle is equal to the real impedance (Z').

Figure 7:
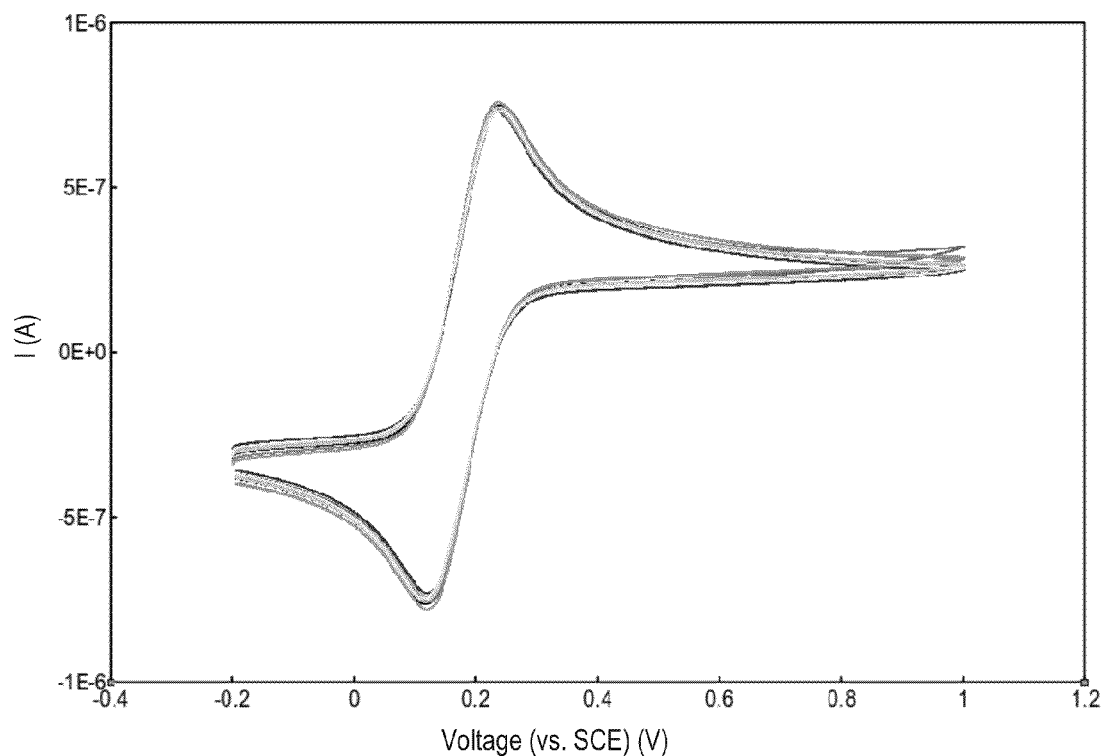
FIG. 7 shows a plot comprising an overlay of cyclic voltammetry measurements of all nine microelectrodes in the 3×3 MEA of the embodiment.

Optical and SEM images, and experimental data, e.g. as shown in FIGS. 1, 2 and 7 demonstrates that the fabrication process provided a 100% process yield, and confirms the feasibility of a reliable wafer-scale fabrication process that utilizes standard semiconductor processes and can be scaled up to N×N arrays (with N up to 100), critical for the development of highly multiplexed biosensor chips.

The cyclic voltammograms of all nine microelectrodes in a chip, using a scan rate of 100 mV/s, are shown in FIG. 7. The electrolyte was 5 mM $Fe(CN)_6^{3-/4-}$ in a 0.01 M PBS buffer.

Figure 8:
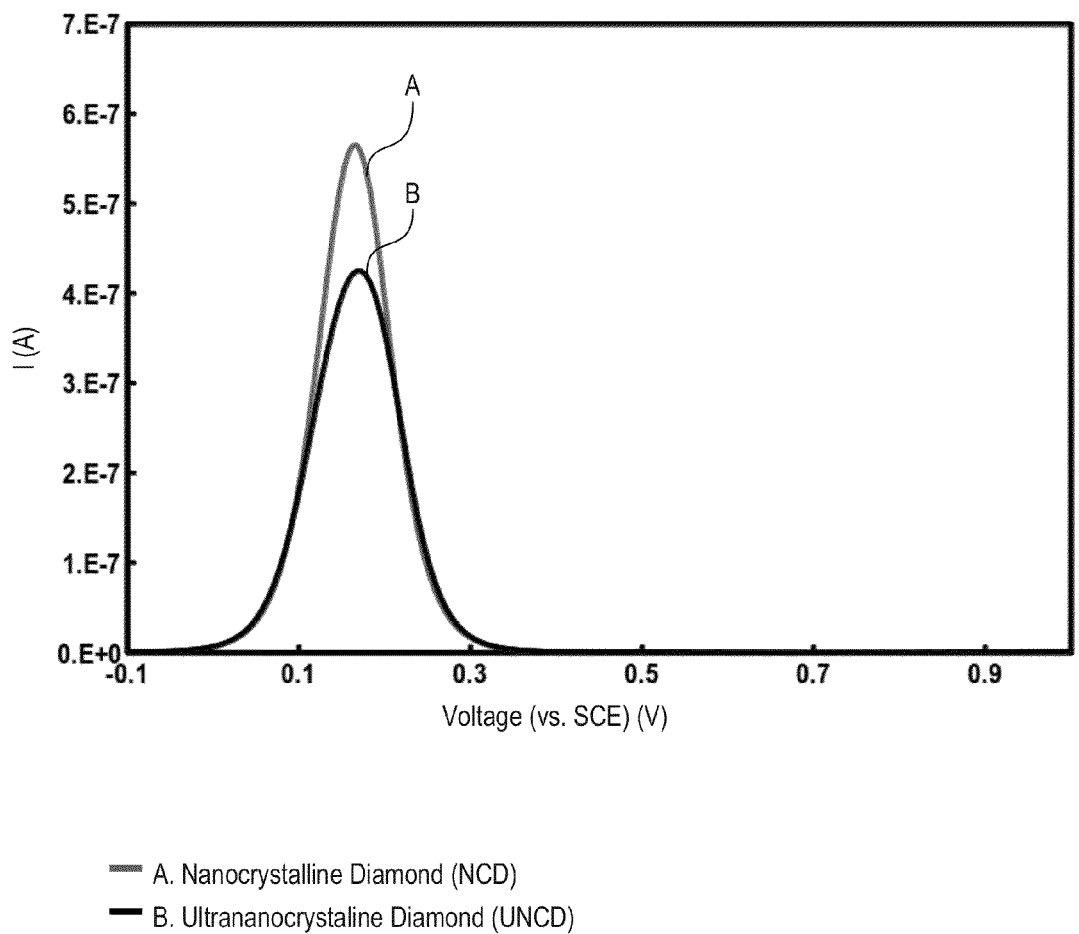
FIG. 8 shows graph comparing differential pulse voltammetry data for an MEA comprising A. NCD microelectrodes and B. UNCD microelectrodes.

For electrochemical sensors, the electrical noise that affects the sensitivity (i.e. the Signal-to-Noise ratio, S/N ratio) can be reduced by employing electrode materials that generate low charging "background" noise. In FIG. 8, it is shown that for diamond electrode materials, the S/N ratio i.e. $I_p/I_b$ is greater than 385 ($I_p$ is peak signal current and $I_b$ is charging "background" current that arises from the presence of surface redox moieties). Line A shows the current vs voltage relationship for NCD while line B shows the current vs voltage relationship for UNCD. In comparison, metal electrodes such as platinum and gold of similar diameters have a S/N of around 40 or less, almost 10× lower than that of the UNCD electrode.

Smaller electrode sizes are well-known to increase faradaic current due to enhanced mass-transport and reduce the non-faradaic "charging" currents. Hence, these smaller electrodes increase the signal-to-noise ratio, i.e. they offer higher sensitivity. By adopting MEAs in the place of an un-patterned macro electrode, a four orders of magnitude increase in sensitivity can be produced. For example: when MEAs were used for bacteria detection, the largest increase in output signal, in this case is charge-transfer resistance, $R_{ct}$ (per unit cfu/mL) after bacteria capture was 17Ω±10% for microelectrodes, as compared to 0.03Ω±10% and 0.005Ω+20% for a shorted array and a continuous film, respectively. This translates into a 17 KΩ change at 1000 cfu/ml, which is comparable to the detection limits of most immunoassays. Further improvements in detection limits (≤10 cfu/ml) can be achieved by decreasing the microelectrode size to 10 μm or less.

The slower electron transfer kinetics and smaller magnitudes of exchange currents of higher resistivity UNCD and NCD as compared to metal electrodes makes the UNCD and NCD surface more electrochemically stable at a wide range of electrochemical potentials and thus makes UNCD and NCD less susceptible to generating electrical background noise.

Thus, referring to the Nyquist plots shown in FIG. 6, for example, the UNCD microelectrodes are observed to generate an EIS spectrum which is close to semi-circular. The semi-circle spectrum obtained from modified UNCD/NCD microelectrodes, i.e. after antibody/casein attachment and bacteria capture, is indicative of the charge-transfer resistance (Rct), which is equal to the diameter of the semi-circle (real part of the impedance spectrum). Thus, this parameter can alone be used as a single parameter for quantifying the number of antibodies and bacteria attached to the surface. This provides a unique advantage for quantifying the detection event selectively.

These properties are new and unexpected for NCD and UNCD microelectrodes as compared to carbon nanotubes and other $sp^2$ carbon-containing electrodes and metal electrodes. The electrode properties of carbon nanotubes are replicated or exceeded when using UNCD or NCD arrays according to embodiments of the invention. In particular, these unique and unexpected properties of higher resistivity (lower conductivity) for NCD and UNCD microelectrodes are particularly apparent when the electrode diameter or linear width is less than 100 microns, and more particularly less than 10 microns. The exchange current improvement for a UNCD MEA in comparison to the less desirable exchange current values on a glassy carbon sensing electrode (GCE) and gold (Au) is apparent in comparing FIGS. 9, 10 and 11.

Figure 9:
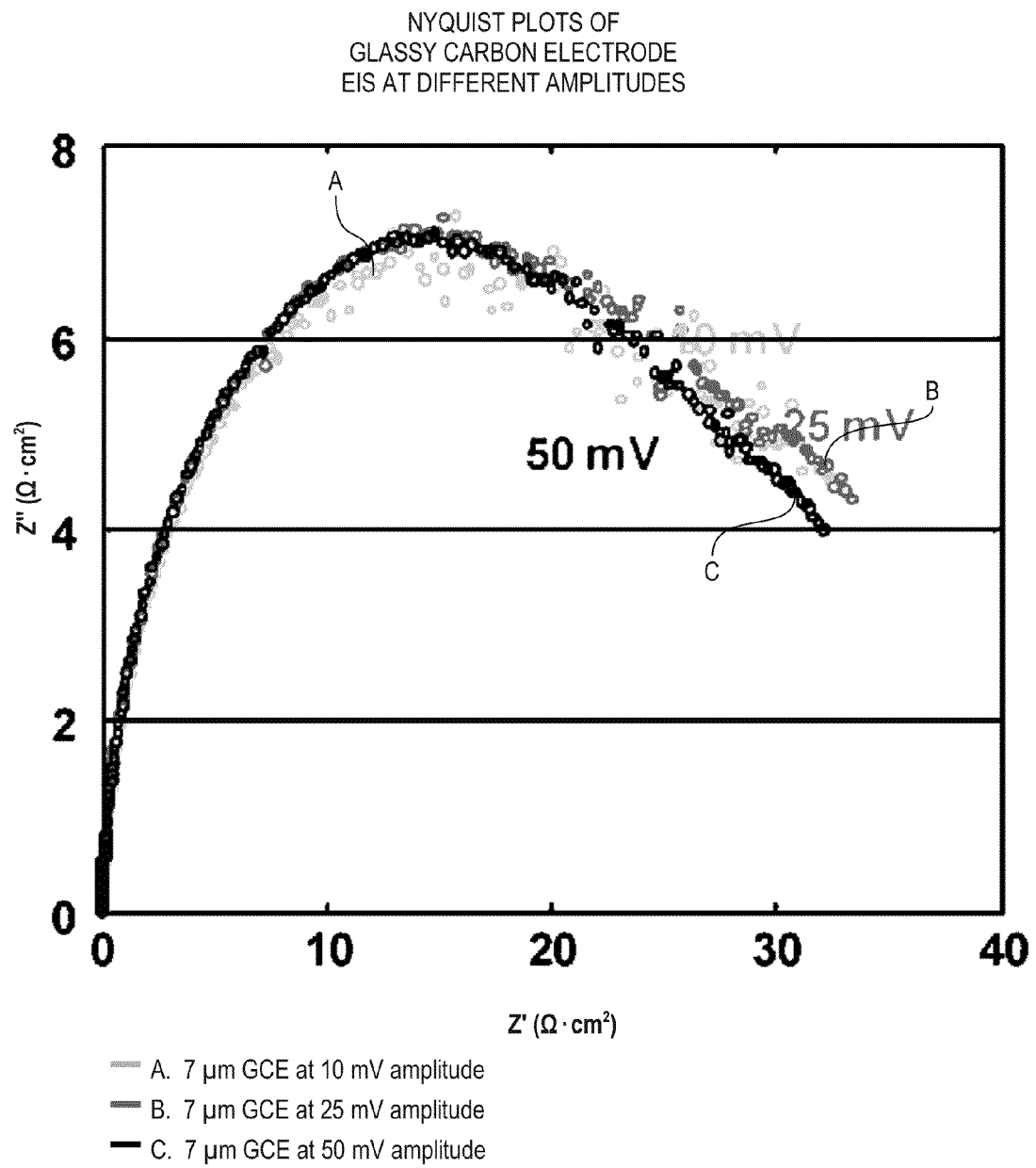
FIG. 9 shows EIS Nyquist plots of a 7 µm glassy carbon electrode (GCE) at different peak voltage amplitudes.

FIG. 9 shows impedance curves of 7 μm GCE with different amplitudes 10, 25, 50 mV (indicators A, B, and C respectively). The solution used was 5 mM $K_4Fe(CN)_6$/5 mM $K_3Fe(CN)_6$ in 0.1 M phosphate buffer (pH 7.4). The EIS spectrum was 0.1 Hz to 100 kHz at 0 VDC vs. SCE. The x-axis represents the real component of the contact impedance while the y-axis represents the imaginary component. With the small electrode size (<10 μm) there is a lot of noise produced in the EIS as shown in the scattered data points of FIG. 9. Electrodes made of other materials including platinum and gold exhibit similar high noise levels for small electrode size (Siddiqui et al., 2010).

Figure 10:
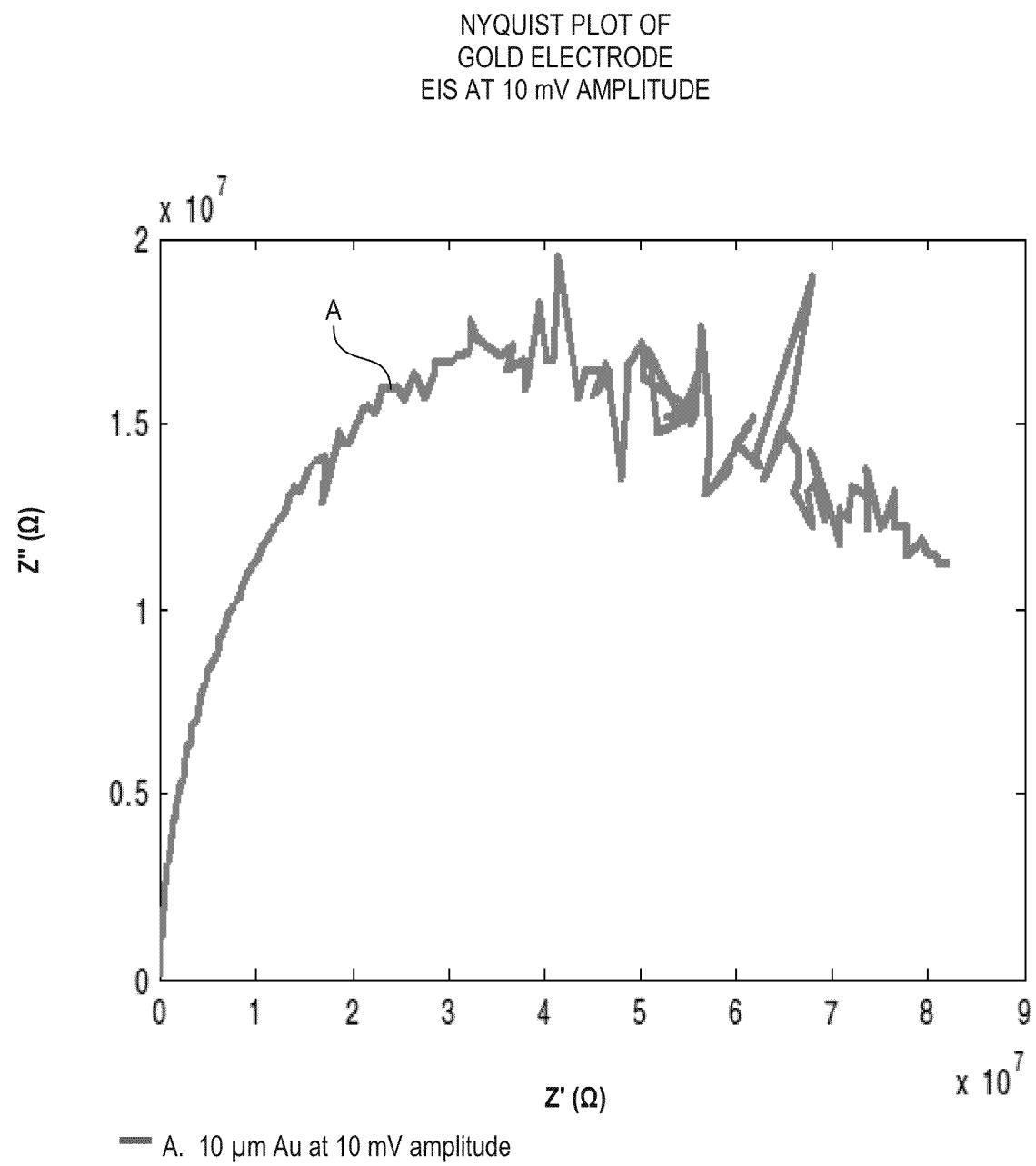
FIG. 10 shows EIS Nyquist plots of 10 µm gold (Au) electrode at a 10 mV amplitude.

FIG. 10 shows an impedance curve for a 10 μm gold electrode which demonstrates the excessive noise produced by the small diameter of the electrode. In this test, the frequency range was between 0.01 Hz to 5 kHz (Bruce et al., 1994).

Figure 11:
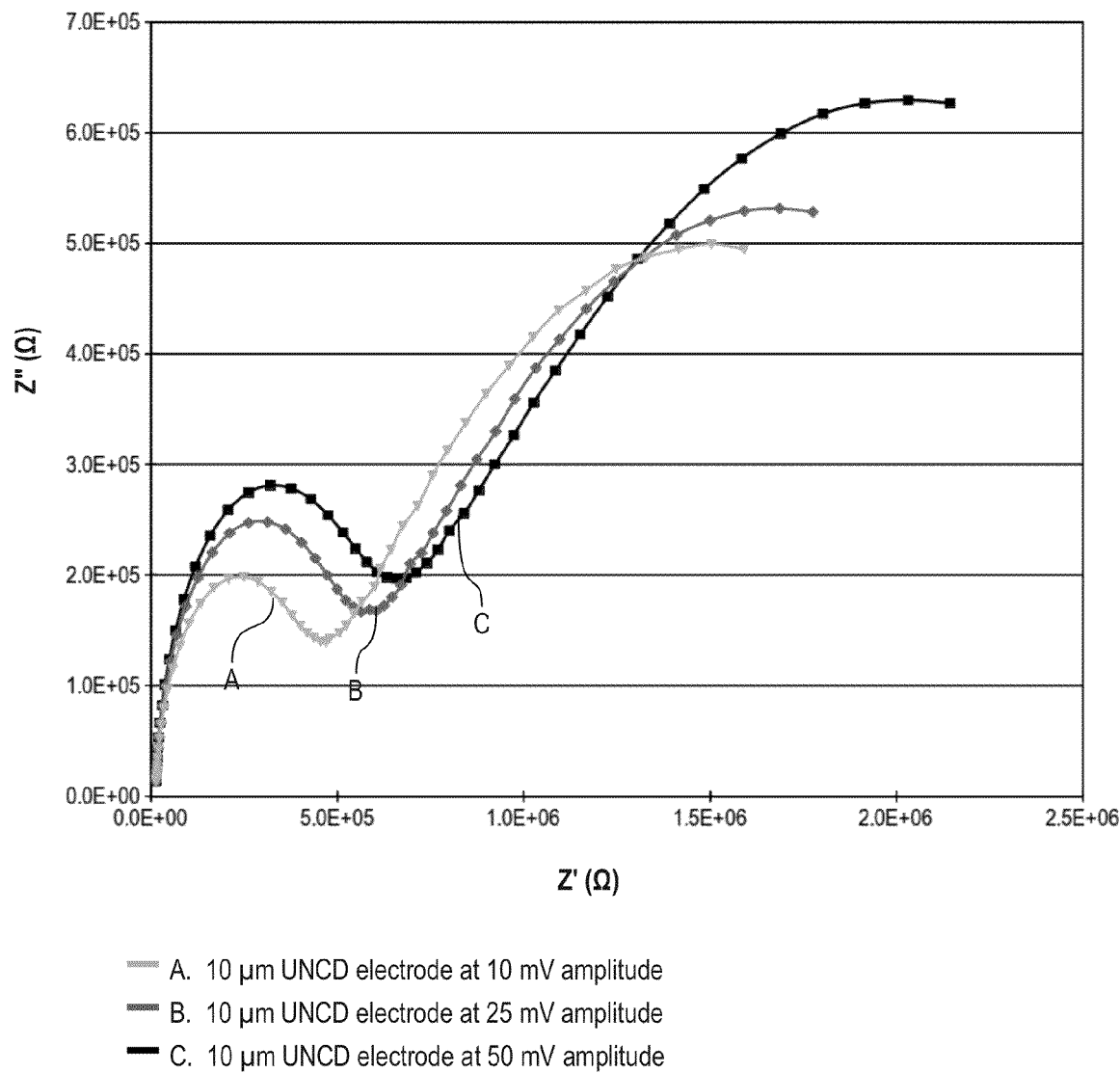
FIG. 11 shows EIS Nyquist plots of a 10 µm UNCD electrode at different peak voltage amplitudes.
Figure 12:
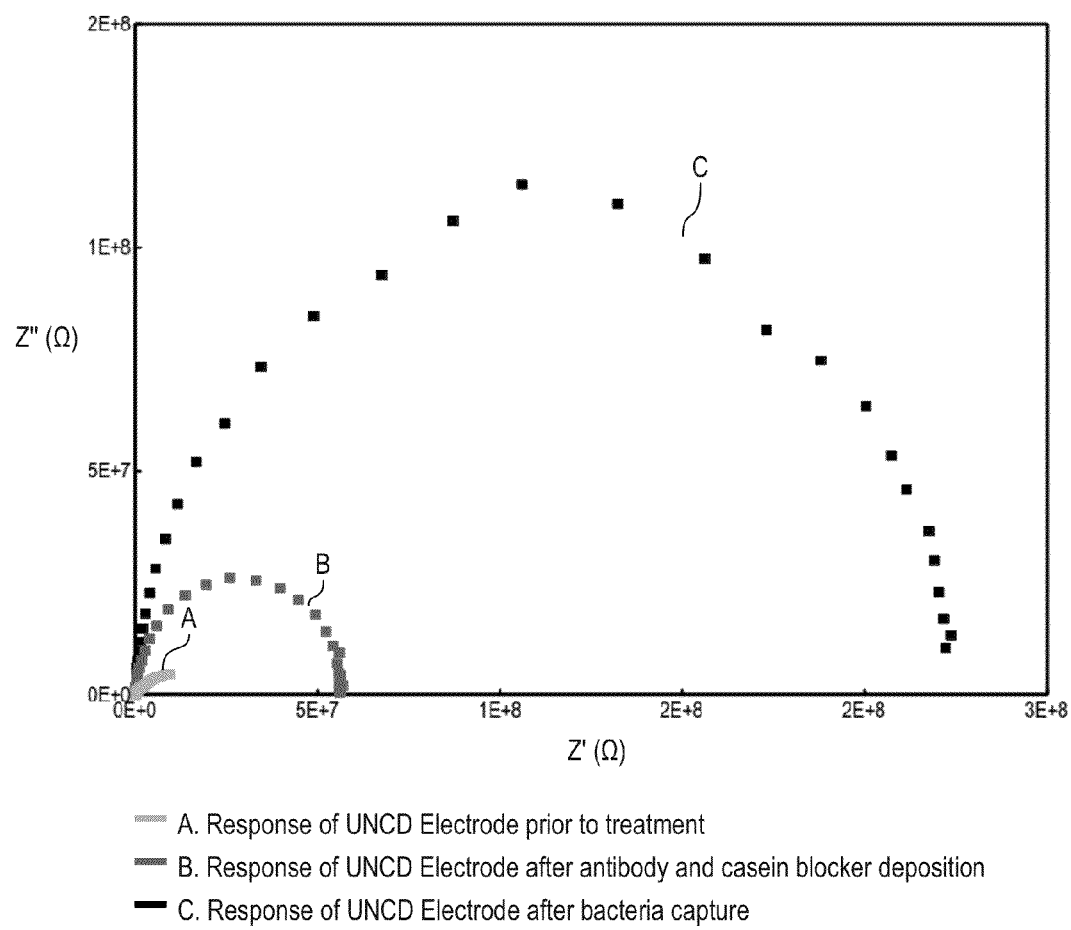
FIG. 12 shows Nyquist plots for electrode 3 of the UNCD MEA of the first embodiment: A) before surface functionalization; B) after surface modification and before bacteria capture; C) and the modified surface after bacteria capture.
Figure 13:
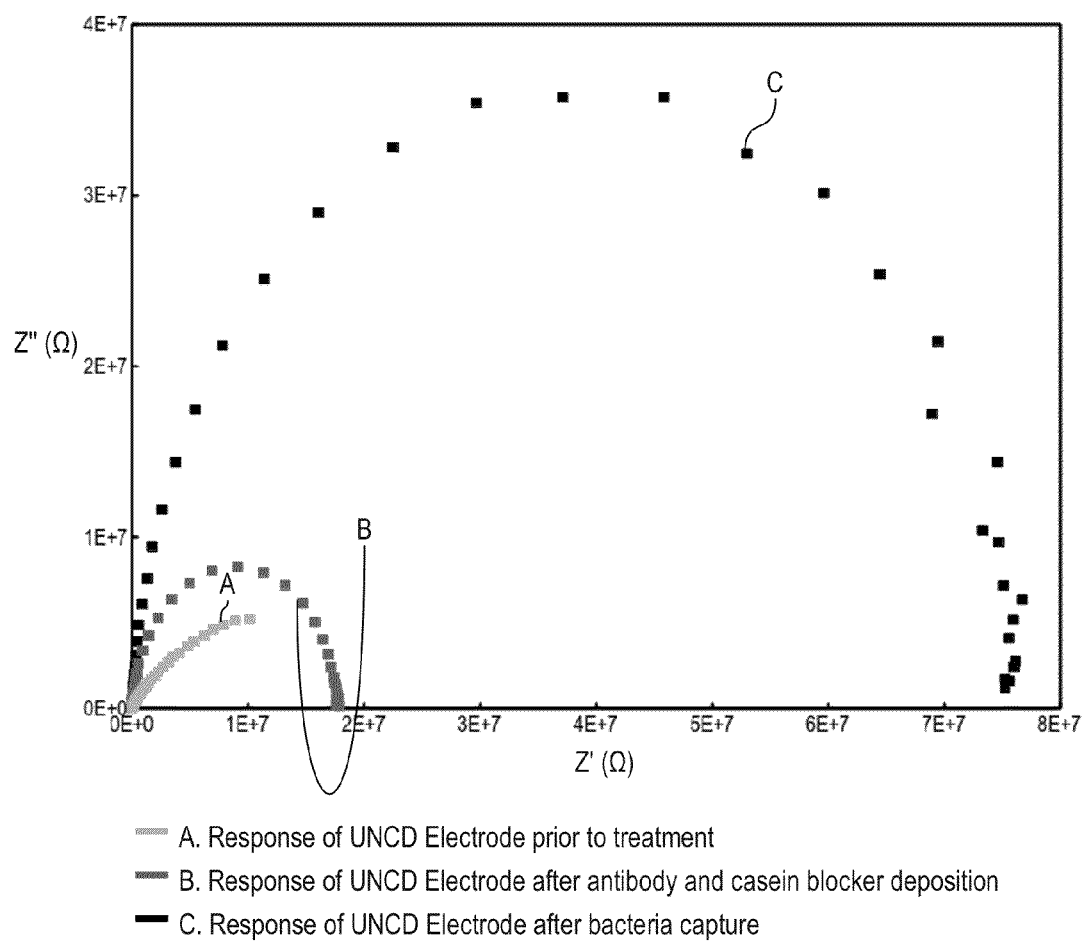
FIG. 13 shows Nyquist plots for electrode 4 of the UNCD MEA of the first embodiment. A) before surface functionalization; B) after surface modification and before bacteria capture; C) and the modified surface after bacteria capture.
Figure 14:
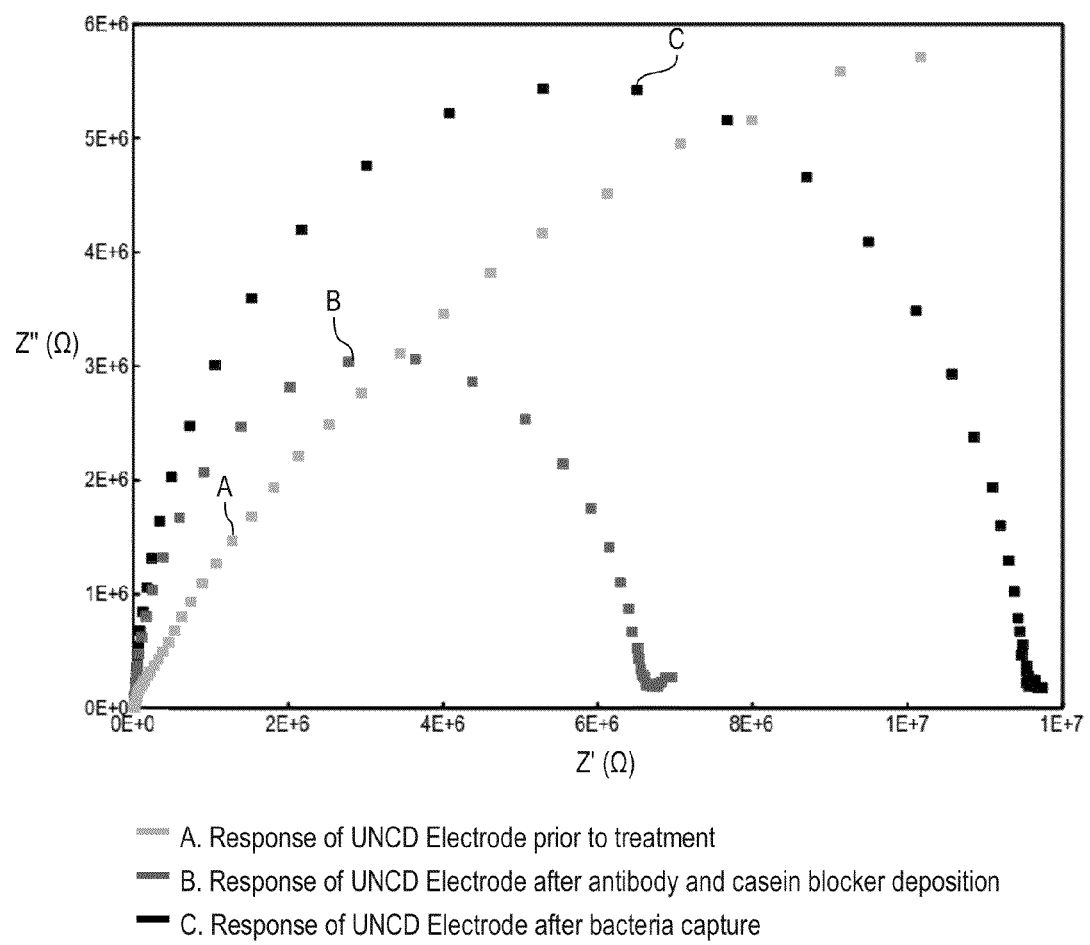
FIG. 14 shows Nyquist plots for electrode 5 of the UNCD MEA of the first embodiment. A) before surface functionalization; B) after surface modification and before bacteria capture; C) and the modified surface after bacteria capture.
Figure 15:
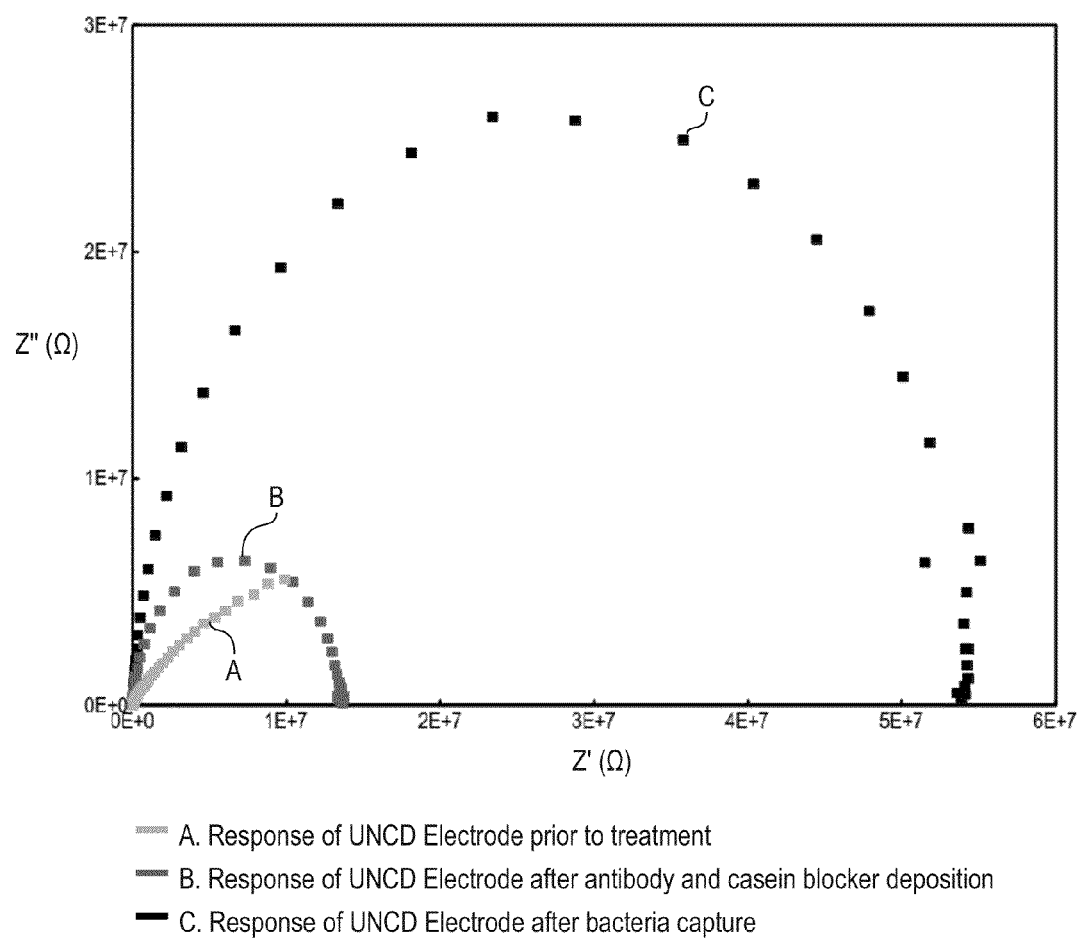
FIG. 15 shows Nyquist plots for electrode 8 of the UNCD MEA of the first embodiment. A) before surface functionalization; B) after surface modification and before bacteria capture; C) and the modified surface after bacteria capture.
Figure 16:
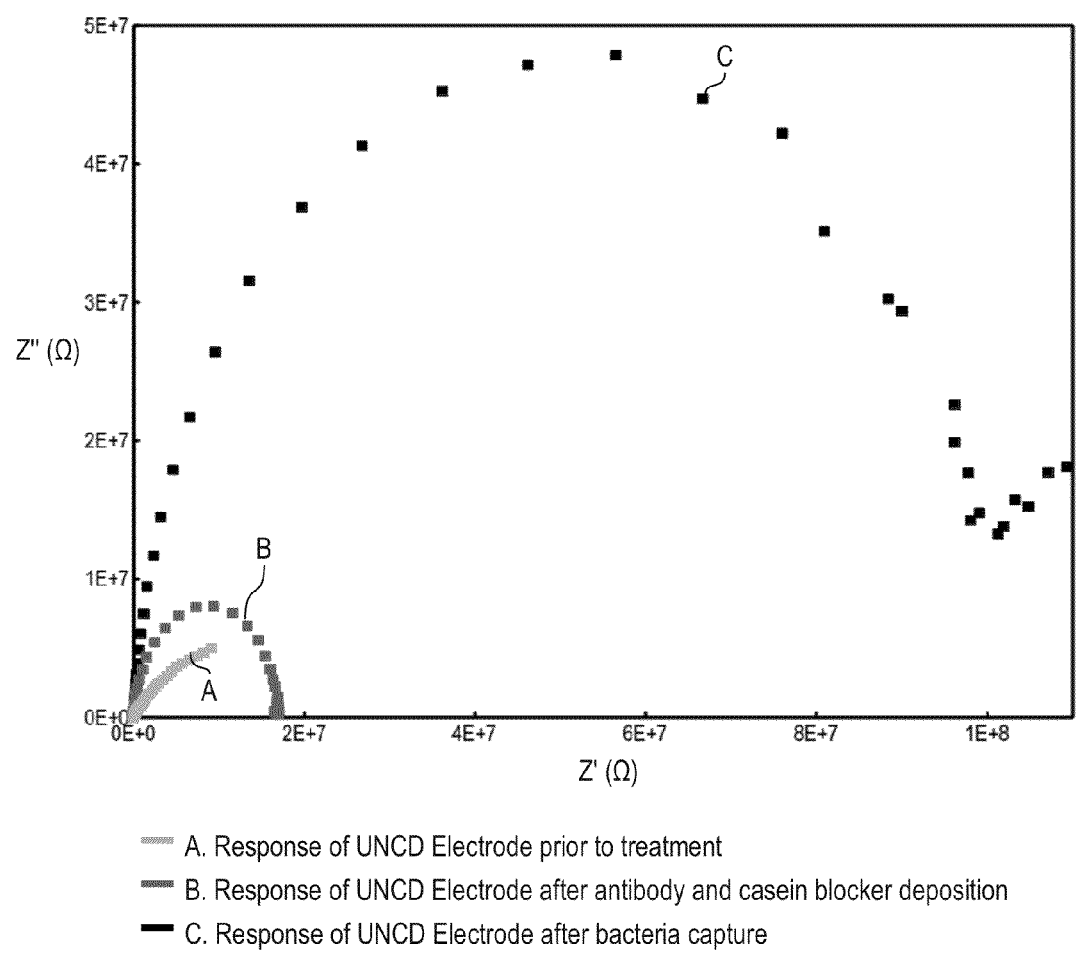
FIG. 16 shows Nyquist plots for electrode 9 of the UNCD MEA of the first embodiment. A) before surface functionalization; B) after surface modification and before bacteria capture; C) and the modified surface after bacteria capture.

In comparison, FIG. 11 shows the impedance curves of a 10 μm UNCD electrode at peak voltage amplitudes of 10, 25, 50 mV (indicators A, B, and C respectively). The solution was similar to that used for the GCE tests with similar spectrum range. However, even with the small electrode size, the EIS curves are very smooth and regular with minimal noise, and notably, the plots follow a substantially semi-circular curve.

The fit of the 10 μm gold electrode to both the Fleischmann and Pons model and the hemispherical model is very good at higher frequencies. However a divergence of up to approximately 8% may be observed at lower frequencies. For noisier spectra, i.e. when the data points are more scattered, it becomes difficult to fit the data to the model and the error or divergence becomes high (Bruce et al., 1994). For the 10 μm UNCD electrode, the divergence or error from these models is less than 4.3%.

As illustrated by FIGS. 9 and 10, it is generally observed that for electrodes made from metals, and non-diamond, carbon-based electrodes, the EIS spectrum comprises a semi-circle accompanied by Warburg-element type behavior after attachment of antibodies and bacteria. The presence of the Warburg-element makes the relationship between charge-transfer resistance and number of antibodies/bacteria attached to the surface non-linear, and thus complicates quantification of number of bacteria attached to the surface. Thus more complex circuit fitting models are required to analyze experimental data.

Thus, when using UNCD electrodes, observance of a semi-circle spectrum, which is believed to be due to unique properties of UNCD, (i.e. slower kinetics and smaller exchange currents), provides a significant advantage for quantification of a detection event. This behavior simplifies modeling. It allows for a single EIS parameter, i.e. the diameter of the semi-circle spectrum or charge transfer resistance, to be used as a highly sensitive quantitative detection measure when using NCD ? and UNCD electrodes.

The exchange current is lower (i.e. improved) for small electrodes of UNCD/NCD relative to carbon nanotubes, carbon nanofibers or metal electrodes. This effect is believed to be at least partly because the conductivity of UNCD/NCD is lower, which increases the interaction time. The conductivity of UNCD/NCD can be easily modified by changes in the doping level during deposition. In addition, carbon nanotube processing is challenging and expensive which is not a problem for diamond depositions which utilize nearly standard semiconductor processing techniques. Finally, UNCD/NCD films are much more stable under electrochemical oxidation stress than either metal or $sp^2$ carbon materials because of the higher oxidative stability of $sp^a$ carbon. This provides further advantages for microarrays according to embodiments of the invention over $sp^2$ carbon and metal electrodes.

Table 1 compares the change in impedance after bacteria capture (i.e. sensitivity) for an un-patterned UNCD, electrically shorted 3×3 UNCD MEA and an electrically isolated (i.e. all nine microelectrodes are electrically individually addressable) 3×3 UNCD MEA. The antibody and bacteria concentrations were fixed at ~50 μg/mL and ~1.0×10⁷ cfu/ml, respectively.

TABLE 1

| Impedance Comparison after Bacteria Capture | |
|---|---|
| Type of UNCD Array | ΔZ/Ω (per cfu/ml) |
| Un-patterned | 0.005 |
| 3x3 array (electrically shorted) | 0.03 |
| 3x3 array (electrically isolated) | 17 |

Table 2 shows the $R_{ct1}$ and $R_{ct2}$ values, which are the charge transfer resistances after antibody/casein and bacteria capture, respectively when a UNCD MEA was used as an impedance biosensor. The $R_{ct2}/R_{ct1}$ ratio gives the value of the change in faradaic impedance after bacteria capture. This ratio must be a constant for all microelectrodes as long as there is no nonspecific binding.

TABLE 2

| Electrode # | $R_{ct1}/R_{ct2}$ |
|---|---|
| 3 | 3.94 |
| 4 | 4.14 |
| 5 | 1.42 |
| 8 | 3.81 |
| 9 | 6.1 |

FIGS. 12 through 16 show Nyquist plots respectively for microelectrodes 3, 4, 5, 8 and 9 of the MEA of the embodiment. In each plot, the least steep curve in each plot (represented by indicator A) is the hydrogen terminated UNCD electrode 101, the mid sloped curve (indicator B) is from the UNCD electrode after surface modification with antibodies 121 and a casein blocker 115 and the curve with the steepest takeoff (indicator C) is from the UNCD electrode after bacteria 131 capture. The electrolyte used was a 5 mM $Fe(CN)_6^{3-/4-}$ in 0.01 M PBS buffer. The antibody and bacteria concentration was ~50 μg/mL and ~$1.0\times10^7$ cfu/ml, respectively.

These results demonstrate high signal reproducibility from these microelectrodes, which is believed to be due to the unique properties of the UNCD interface, such as its chemical stability and ultra-smooth surface morphology. These properties help to provide a more uniform, dense and conformal coverage of monolayers and casein and minimal nonspecific binding. These unique properties contribute to a relatively high and constant signal reproducibly, relative to other electrode materials.

As described above, it is believed that these advantages arise from unique characteristics of lower conductivity NCD and UNCD electrodes. Typically, these nanocrystalline diamond layer comprises $sp^3$ diamond grains with $sp^2$ diamond grain boundaries.

INDUSTRIAL APPLICABILITY

As described above, NCD and UNCD electrodes comprising ultrasmooth boron or nitrogen doped $sp^3$ conductive diamond surfaces, and particularly modified electrodes for electrical signal transduction, are demonstrated to exhibit significantly exhibit substantial increases in sensitivity, selectivity and signal reproducibility relative to conventional metal electrodes, and because of their high surface stability, they show minimal surface fouling. In particular, for a given geometric area, UNCD and NCD surfaces as described above exhibit lower background currents (i.e. 10× lower) and thus exhibit improved sensitivity as compared to metal electrodes.

Notably, for electrochemical impedance spectroscopy, nanocrystalline diamond microelectrodes comprising NCD or UNCD electrodes have been shown to generate a semi-circle-spectrum which provides for quantitative detection of a biological or chemical target based on a single EIS parameter defined by a charge transfer resistance ($R_{ct}$) determined from said semicircle-spectrum.

Thus, ultra-smooth (<20 nm RMS), ultra-small (100 nm-100 μm) UNCD/NCD electrodes in array format offer a robust electrochemical platform in terms of reproducibility, selectivity and sensitivity. In addition, for detection applications such a platform would reduce the total number of experiments and lower the cost per detection.

For example, it is proposed that a NCD or UNCD microelectrode array (MEA) can be used to determine the average limiting values of all these parameters for different concentrations of antigens by performing repetitive experiments in the laboratory. Once these limiting values are determined, they can be used to distinguish between a real detection signal and that due to nonspecific binding or any other unexpected events or errors during the bio-functionalization process. Therefore, the need for control experiments is significantly reduced in view of the unique properties of the NCD and UNCD interface, such as its chemical stability and minimal nonspecific binding and high binding capacity, in samples that are prepared with minimal processing complexity.

Although embodiments of the invention have been described and illustrated in detail, it is to be clearly understood that the same is by way of illustration and example only and not to be taken by way of limitation, the scope of the present invention being limited only by the appended claims.

REFERENCES

S. Siddiqui, Z. Dai, C. J. Stavis, H. Zheng, N. Moldovan, R. J. Hamers, J. A. Carlisle and Prabhu U. Arumugam, "A quantitative study of detection mechanism for a label-free impedance biosensor using ultrananocrystalline diamond microelectrode array" *Biosensors and Bioelectronics*, 35, 1, 15 May 2012, Pages 284-290.

Shabnam Siddiqui, Prabhu U. Arumugam, Hua Chen, Jun Li, and M. Meyyappan, "*Characterization of Carbon Nanofiber Electrode Arrays Using Electrochemical Impedance Spectroscopy: Effect of Scaling Down Electrode Size*", *ACS Nano*, 2010 4 (2), 955-961

Bruce, P. G., Lisowska-Oleksiak, A., Los, P. & Vincent, C. A. "*Electrochemical impedance spectroscopy at an ultramicroelectrode.*" *J. Electroanal. Chem.* 367, 279-283

Holm-Kennedy, James W. "Ultrasensitive biosensors." U.S. Pat. No. 7,692,219. 6 Apr. 2010.

Hengstenberg, Andreas, and Peter Tschuncky. "Open electrochemical sensor" U.S. Pat. No. 7,758,735. 20 Jul. 2010.

Sommer, Sabrina, Herbert Kiesele, and Frank Mett. "Electrochemical sensor having a mediator compound." U.S. Pat. No. 7,883,611. 8 Feb. 2011.

Jiang, Li, et al. "Electro-chemical sensor" U.S. Pat. No. 7,901,555. 8 Mar. 2011.

The invention claimed is:

1. An electroanalytical sensor comprising at least one electrode, each electrode comprising:
   a layer of conductive nanocrystalline diamond (NCD) having a resistivity of >0.05 Ωcm and a surface having a surface roughness of <20 nm Ra (arithmetic mean value), wherein the layer of conductive nanocrystalline diamond comprises ultrananocrystalline diamond (UNCD) having an average grain size of <10 nm.

2. An electroanalytical sensor according to claim 1 wherein the UNCD has a surface roughness of <10 nm Ra.

3. An electroanalytical sensor according to claim 1 wherein the UNCD comprises boron or nitrogen doped UNCD.

4. An electroanalytical sensor according to claim 1 wherein the surface of the electrode is hydrogen terminated.

5. An electroanalytical sensor according to claim 4 wherein the hydrogen terminated surface is bio-functionalized.

6. An electroanalytical sensor according to claim 4 wherein the hydrogen terminated surface further comprises a surface modification comprising attachment of sensing molecules for detection of a specific biological or chemical target and a coating of a blocking layer for reducing non-specific binding of the target.

7. An electroanalytical sensor according to claim 6, wherein the layer of conductive nanocrystalline diamond is patterned to form a microelectrode array comprising a plurality of diamond microelectrodes each having an active area defined by a diameter or lateral dimension, wherein the diameter or lateral dimension is matched to the size of the biological or chemical target to be detected.

8. An electroanalytical sensor according to claim 6 for detection of an *E. coli* bacterium by electrochemical impedance spectroscopy, wherein the sensing molecules comprise an *E. coli* antibody and the blocking layer comprises a casein blocking layer.

9. An electroanalytical sensor according to claim 1 wherein the layer of conductive nanocrystalline diamond is patterned to form a microelectrode array comprising a plurality of diamond microelectrodes, each having an active area defined by a diameter or lateral dimension, wherein the diameter or lateral dimension is in the range of: 1 mm or less; or 100 μm or less; or 100 nm to 10 μm.

10. An electroanalytical sensor according to claim 9 wherein the spacing between the microelectrodes is between 1 and 6 times said diameter or lateral dimension of the microelectrodes.

11. An electroanalytical sensor according to claim 9 wherein the number of microelectrodes is between 1 and 10,000.

12. An electroanalytical sensor according to claim 9 further comprising conductive interconnections for electrically addressing each microelectrode individually.

13. An electroanalytical sensor according to claim 9 wherein the layer of NCD or UNCD has a thickness greater than 500 nm.

14. An electroanalytical sensor according to claim 9 further comprising a passivation layer overlying the patterned layer of conductive nanocrystalline diamond defining said microelectrodes and providing isolation between the microelectrodes.

15. An electroanalytical sensor according to claim 14 wherein said isolation layer comprises a dielectric comprising one of: non-conductive diamond; silicon dioxide or other dielectric oxide; silicon nitride or other dielectric nitride; polymers selected from the group consisting of PDMS, SU-8, parylene and other suitable polymers.

16. An electroanalytical sensor according to claim 15 wherein the passivation layer has a thickness greater than 500 nm, and defines an electrochemical microcell over each microelectrode.

17. An electroanalytical sensor according to claim 1 wherein the nanocrystalline diamond layer comprises sp3 diamond grains with sp2 diamond grain boundaries.

18. An electroanalytical sensor comprising: a microelectrode array comprising a plurality of conductive diamond microelectrodes wherein each electrode comprises a layer of conductive nanocrystalline diamond having a resistivity of >0.05 Ωcm and a surface roughness of <20 nm Ra, wherein the layer conductive nanocrystalline diamond comprises ultrananocrystalline (UNCD) diamond having an average grain size of <10 nm.

19. An electroanalytical sensor according to claim 18 wherein each microelectrode comprises an active area having a diameter or lateral dimension of between 100 nm and 1 mm.

20. An electroanalytical sensor according to claim 18 configured for use for electrochemical impedance spectroscopy.

21. A method of electrochemically sensing a biological or chemical target by electrochemical impedance spectroscopy using an electroanalytical sensor as defined in claim 18, wherein detecting a change in impedance comprises applying an alternating voltage signal having a peak amplitude greater than 10 mV.

22. The method of claim 21 wherein the signals has a frequency in the range from 1 Hz to 750 kHz.

23. The method of claim 21 providing a signal-to-noise ratio of greater than 300.

24. The method of claim 21 wherein the nanocrystalline diamond microelectrodes comprise NCD or UNCD electrodes generating a semicircle-spectrum and wherein quantitative detection is based on a single EIS parameter defined by a charge transfer resistance (Rct) determined from said semicircle-spectrum.

25. A method of fabricating a microelectrode array for an electrochemical biosensor, comprising:
providing a substrate;
providing thereon a layer of conductive diamond comprising nanocrystalline diamond having a resistivity of >0.050 Ωcm and a surface having a surface roughness of <20 nm Ra,
patterning the diamond layer to define a plurality of microelectrodes;
depositing thereon a dielectric passivation layer and opening apertures in the passivation layer over each microelectrode to expose the surface of each microelectrode; and
surface treating each microelectrode to provide a hydrogen terminated surface.

* * * * *